United States Patent
Clayman et al.

(10) Patent No.: US 6,716,183 B2
(45) Date of Patent: Apr. 6, 2004

(54) GUIDEWIRE

(75) Inventors: Ralph V. Clayman, Clayton, MO (US); Edward D. Pingleton, Laguna Niguel, CA (US); Frans Vandenbroek, Rancho Santa Margarita, CA (US); Ghassan Sakakine, Mission Viejo, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 09/947,071

(22) Filed: Sep. 5, 2001

(65) Prior Publication Data

US 2002/0010426 A1 Jan. 24, 2002

Related U.S. Application Data

(63) Continuation of application No. PCT/US00/11586, filed on Apr. 28, 2000.
(60) Provisional application No. 60/132,055, filed on Apr. 30, 1999.

(51) Int. Cl.$^7$ ............................................. A61M 25/09
(52) U.S. Cl. ....................................................... 600/585
(58) Field of Search ................................ 600/433–435, 600/585; 604/523–533

(56) References Cited

U.S. PATENT DOCUMENTS

| | | | |
|---|---|---|---|
| 3,612,058 A | 10/1971 | Ackerman | 128/348 |
| 3,625,200 A | * 12/1971 | Muller | 600/585 |
| 4,682,607 A | 7/1987 | Vaillancourt et al. | 128/772 |
| 4,748,986 A | 6/1988 | Morrison et al. | 128/772 |
| 4,884,579 A | 12/1989 | Engelson | 128/772 |
| 5,001,825 A | 3/1991 | Halpern | 29/456 |
| 5,067,489 A | 11/1991 | Lind | 128/772 |
| 5,129,890 A | 7/1992 | Bates et al. | 604/281 |
| 5,217,026 A | 6/1993 | Stoy et al. | 128/772 |
| 5,228,453 A | 7/1993 | Sepetka | 128/772 |
| 5,238,004 A | 8/1993 | Sahatjian et al. | 128/772 |
| 5,333,620 A | 8/1994 | Moutafis et al. | 128/772 |
| 5,363,847 A | 11/1994 | Viera | 128/657 |
| 5,433,200 A | 7/1995 | Fleischhacker, Jr. | 128/657 |
| 5,443,907 A | 8/1995 | Slaikeu et al. | 428/375 |
| 5,449,369 A | 9/1995 | Imran | 606/159 |
| 5,452,726 A | 9/1995 | Burmeister et al. | 128/772 |
| 5,497,782 A | 3/1996 | Fugoso | 128/772 |
| 5,551,443 A | 9/1996 | Sepetka et al. | 128/772 |
| 5,720,300 A | 2/1998 | Fagan et al. | 128/772 |
| 5,722,424 A | 3/1998 | Engelson | 128/772 |
| 5,749,837 A | 5/1998 | Palermo et al. | 600/585 |
| 5,756,144 A | 5/1998 | Wolff et al. | 427/2.3 |
| 5,769,796 A | 6/1998 | Palermo et al. | 600/585 |
| 5,772,609 A | 6/1998 | Nguyen et al. | 600/585 |
| 5,827,201 A | 10/1998 | Samson et al. | 600/585 |
| 5,840,046 A | 11/1998 | Deem | 600/585 |
| 5,876,356 A | 3/1999 | Viera et al. | 600/585 |

* cited by examiner

Primary Examiner—Max F. Hindenburg
Assistant Examiner—David J. McCrosky
(74) Attorney, Agent, or Firm—Richard L. Myers

(57) ABSTRACT

A urological guidewire includes a core formed of a first metallic material and extending toward an end of the guidewire. A coil having a plurality of convolutions is disposed around the core at the end of the guidewire, the coil being formed of a second metallic material different than the first metallic material. A mechanical interlock is formed to inhibit separation of the different materials forming the coil and the core. The mechanical interlock may include an enlargement at the end of the core and a bonding material fixing the enlargement to the coil. The convolutions may include a penultimate convolution with a first radius of curvature and an ultimate convolution having a second, shorter radius of curvature to form a bridge. In this case, portions of the core can be bent back on themselves and directed over or around the bridge to form the mechanical interlock.

12 Claims, 5 Drawing Sheets

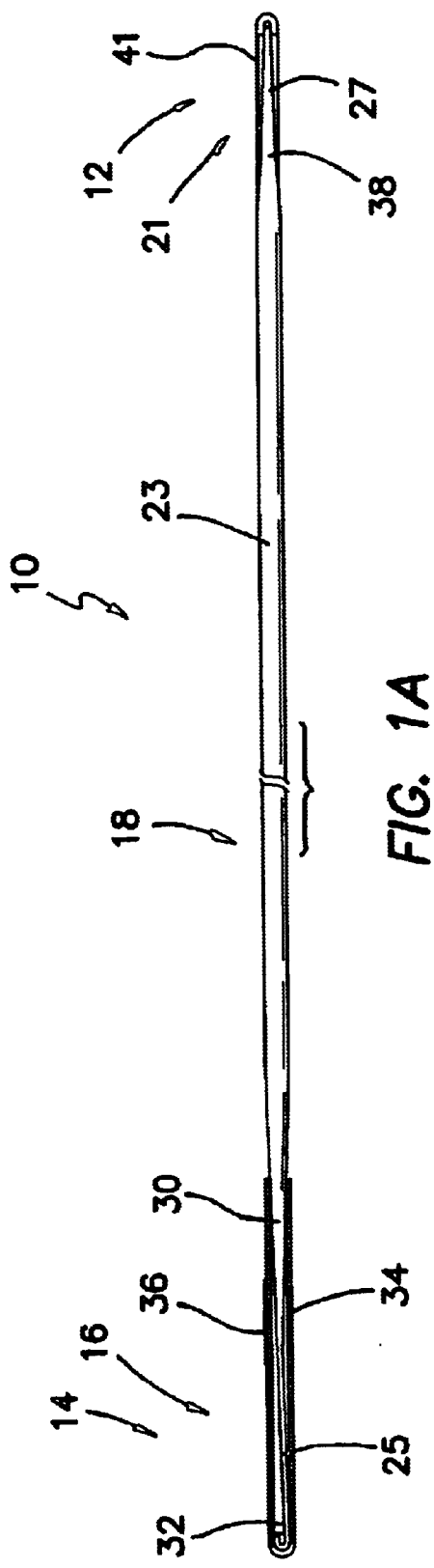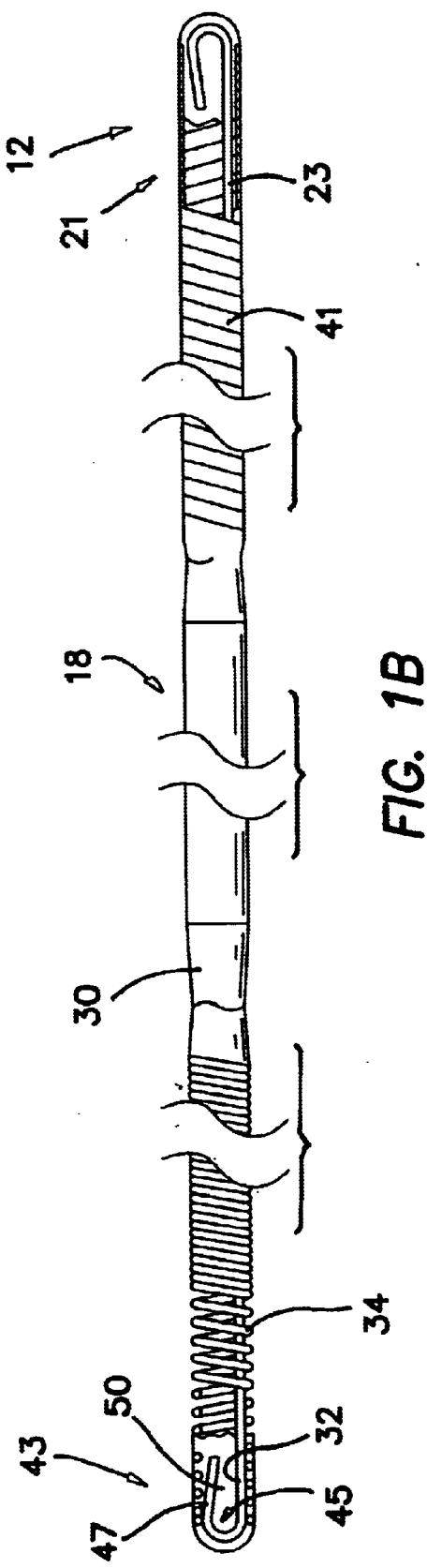

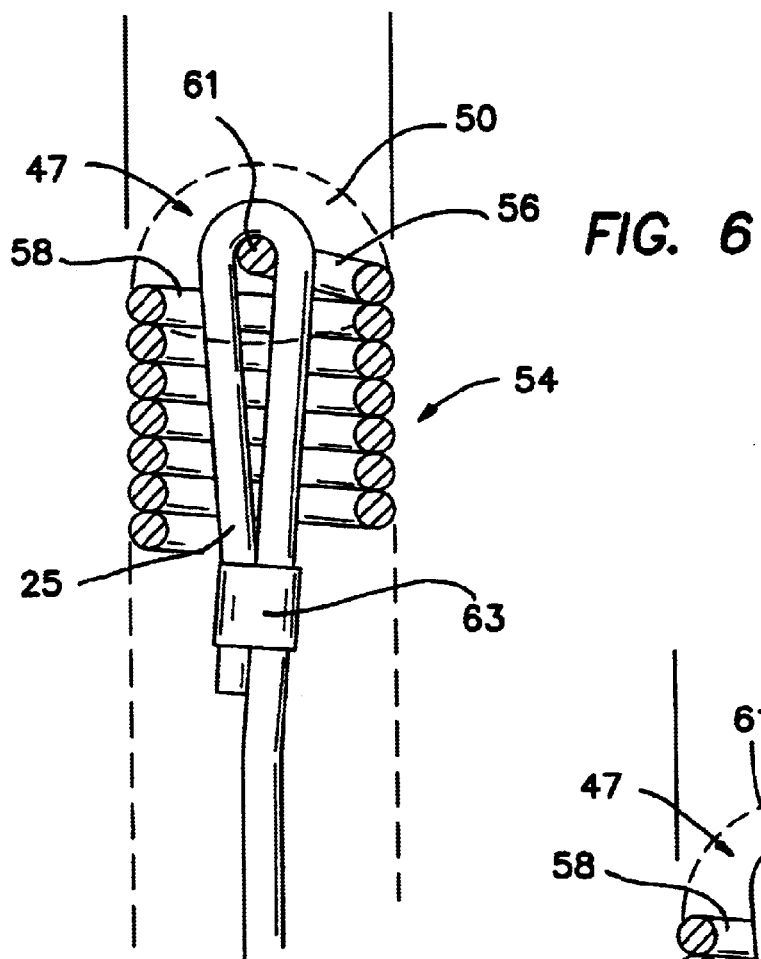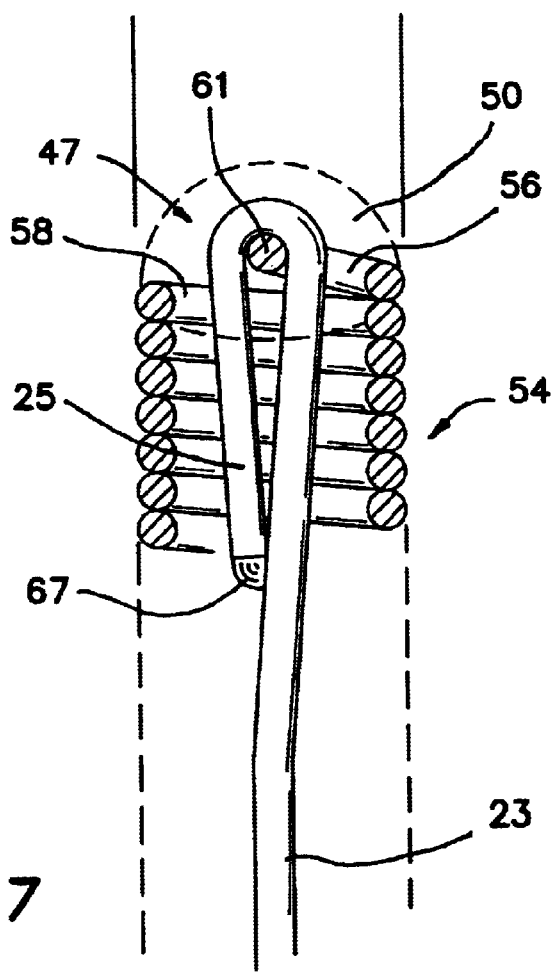
FIG. 6
FIG. 7

GUIDEWIRE

This application is a continuation of PCT Application No. PCT/US00/11586, filed Apr. 28, 2000, which claims the benefit of U.S. Provisional Application No. 60/132,055, filed Apr. 30, 1999.

BACKGROUND OF THE INVENTION

1. Field of the Invention

This invention relates generally to guidewires and, more specifically, to urological guidewires adapted for insertion and instrument guidance through the urological conduit.

2. Discussion of Related Art

The first step in a typical endoscopic urological procedure is placement of a guidewire into the patient's urological system. When operatively disposed, the guidewire typically extends from outside the patient, through the urethra, the bladder, the ureter, and into the kidney. The guidewire allows a variety of specialized tools, such as catheters and endoscopes, to be repeatedly positioned in the urological system with ease, safety, and efficiency.

Urological guidewires of the past have typically been provided with properties relating to flexibility, lubricity, and stiffness. Each guidewire has tended to emphasize one of these properties along its entire length, in order to provide certain advantages at different points in the procedure. For example, due to the serpentine configuration of a ureter, the initial or "access" guidewire is required to have a high degree of flexibility to facilitate easy insertion. However, once the flexible access guidewire is in place, it is ill-suited for the placement of instruments. By comparison, stiffer guidewires facilitate the insertion of instruments, because they tend to straighten out the anatomy in a way that flexible guidewires cannot. By straightening the anatomy and providing a more rigid guide element, instruments can be more easily inserted over the guidewire to reach an operative site.

In the past, before instrumentation could be inserted into the patient, the flexible access guidewire had to be exchanged for a stiffer, "working" guidewire. This was accomplished by placing an exchange sheath (a small-diameter flexible tube) over the access guidewire and then removing the access guidewire, leaving the sheath in place in the urological system. After the access guidewire was removed from the sheath, the stiffer, working guidewire was then inserted into the exchange sheath and the sheath removed. This left the working guidewire in place of the previous access guidewire. Unfortunately, this four-step procedure was required every time one guidewire was exchanged for another guidewire.

In some cases, the flexible access guidewire was incapable of being fully inserted, typically due to some obstruction such as a urological stone or stricture in the urological system. Under these circumstances, it became desirable to substitute a "slippery" guidewire for the access guidewire. The slippery guidewire provided a high degree of lubricity, typically due to a specialized hydrophilic coating, which facilitated placement past the obstruction. Again, the four-step exchange procedure was required to insert the slippery guidewire. In some cases, the four-step procedure was required to replace the slippery guidewire, perhaps with the access guidewire, in order to achieve the ultimate, desired position within the urological system. Finally, the four-step replacement procedure would then be required once more to replace the access guidewire with the working guidewire.

Alternatively, in those cases where the slippery guidewire was able to achieve the ultimate, desired position in the urological system, it also presented disadvantages for the placement of instrumentation. Slippery guidewires tend to be so lubricious that they can actually fall out of the urological system, purely due to gravitational forces. Under these circumstances, the entire guidewire-placement procedure must be restarted. Accordingly, even with a slippery guidewire in place, it required the four-step, replacement procedure to substitute the working guidewire before the placement of instrumentation could begin. It can be appreciated that in some cases a minimum of three guidewires were needed, along with multiple applications of the four-step procedure for the exchange of the guidewires.

A common method of joining two metals is welding, soldering, or bonding via an adhesive. In the case of a urological guidewire, a metal mandrel, or core, is often joined to a coaxially-oriented metal coil by these methods. These processes are very operator dependent, and if not properly accomplished, can result in separation of the joined components within the patient.

SUMMARY OF THE INVENTION

The present invention overcomes these deficiencies of the prior art and provides a guidewire with a highly flexible, kink-resistant tip providing easy access. This tip can be coated with a lubricious, hydrophilic compound which facilitates passing the guidewire beyond stones and obstructions. A central area of the guidewire features a stiff construction which facilitates the passage of instruments over the guidewire. A proximal portion is provided with moderate flexibility which facilitates the retrograde threading of the guidewire into the guidewire channel of an instrument.

The distal floppy tip of the guidewire consists of a kink-resistant tapered Nitinol core which is covered with a small-diameter stainless steel coil. A method for attaching these two dissimilar metals is achieved with a mechanical locking feature. This mechanical lock is stronger than welding, soldering, braising, or gluing. Nevertheless, a small amount of solder or adhesive can be used to cover and encapsulate the mechanical lock. This process reduces the dependency on a welded or glued joint by replacing the joint with a mechanical interlock. The interlock can still be encapsulated by weld, solder, or adhesive, but the majority of the strength of the joint is now provided by the two parent materials. This method is particularly useful in cases where the components to be joined are made of dissimilar metals. The strength of the resulting joint is of significant advantage to the guidewire and greatly increases the safety of the procedure.

In a preferred embodiment, the urological guidewire has three regions of specific flexibility. The distal region includes a floppy distal tip with a very low coefficient of friction making it relatively slippery. A central section of the guidewire is relatively non-slippery, thereby facilitating the passage of instrumentation, while a proximal section is provided with a medium degree of lubricity. Materials such as Nitinol stainless steel, platinum, gold, and silver can be used in the various sections. A mechanical lock forged between dissimilar metals can be encapsulated in urethane, solder, adhesive, or by insert-molding a polymer.

In one aspect, the invention includes a urological guidewire having a distal section with a first flexibility, a first lubricity, and a first length. A central section is also provided, which has a second flexibility, a second lubricity, and a second length. On the side of the central section opposite the distal section, a proximal section has a third flexibility, a third lubricity, and a third length. The third flexibility is greater than the second flexibility, but less than the first flexibility. The second lubricity and the third lubricity are less than the first lubricity. Finally, the first length is greater than the third length and less than the second length.

In another aspect of the invention, the urological guidewire includes a core formed of the first metallic material and extending toward an end of the guidewire. A coil including a plurality of convolutions extends around the core at the end of the guidewire and is formed of a second metallic material different than the first metallic material. A mechanical interlock is formed between the coil and the core to inhibit separation of the coil from the core. This mechanical interlock can include an enlargement having a lateral dimension greater than the diameter of the core at the distal end of the core. A bonding material encapsulates the enlargement and bonds the enlargement to the coil.

The mechanical interlock can also be formed by providing the coil with a penultimate convolution having a first radius, and an ultimate convolution having a second radius less than the first radius to form a bridge. Portions of the core can be bent over or around the bridge to form the mechanical interlock.

In an associated method of manufacture, the enlargement of the core can be mechanically bonded to the coil. Alternatively, the coil can be provided with the bridge and the core can be bent over or around the bridge and fixed to itself to form a mechanical interlock. These and other features and advantages of the invention will be more apparent with a discussion of preferred embodiments and reference to the associated drawings.

BRIEF DESCRIPTION OF THE DRAWINGS

FIG. 1A is a side elevation view of a urological catheter having a core and a coil extending between a proximal end and a distal end, with a mechanical interlock formed between the core and coil at the distal end;

FIG. 1B is an enlarged side elevation view of the embodiment of FIG. 1A;

FIG. 6 is a side elevation view of the distal end of a core bent back on itself and fixed to itself by a female;

FIG. 7 is an additional embodiment of the core bent back on itself and fixed to itself with a butt joint;

DETAILED DESCRIPTION OF THE PREFERRED EMBODIMENTS AND BEST MODE OF THE INVENTION

Figure 2:
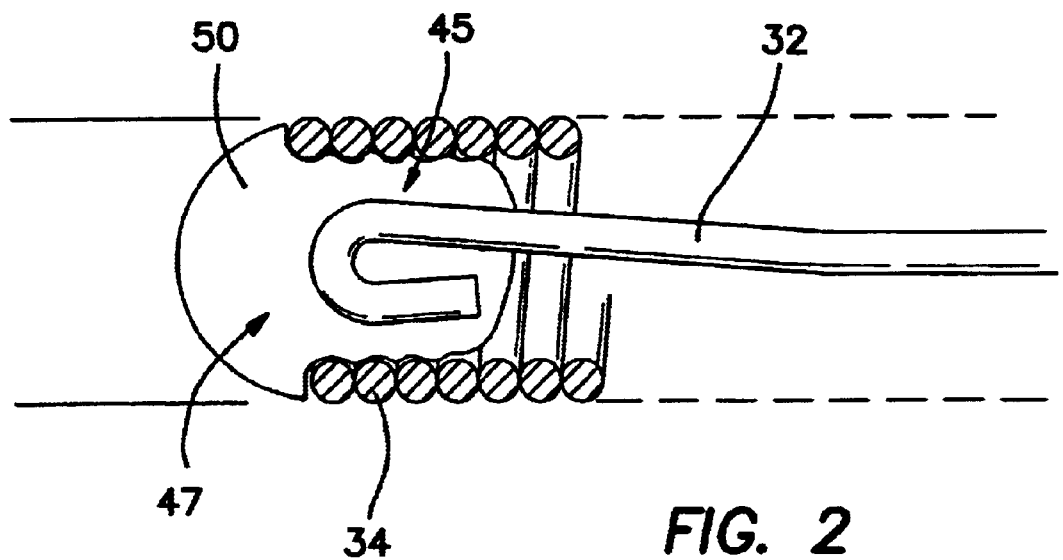
FIG. 2 is an enlarged side elevation view of one embodiment of a mechanical interlock between the core and coil.

A urological guidewire, as illustrated in FIG. 1, and designated generally by the reference numeral 10. The guidewire 10 has an elongate configuration and stems between a proximal end 12 and a distal end 14. The guidewire 10 is adapted for use in accessing distal locations within the urinary tract by inserting the distal end 14 into the urethra of the patient and advancing the distal end 14 to the operative site. Various instruments can then be advanced over the guidewire 10 to perform an operative procedure at the operative site.

In the illustrated embodiment, the urological guidewire 10 includes a distal section 16 with a first flexibility, a first lubricity, and a first length. The central section 18 has a second flexibility, a second lubricity, and a second length. Similarly, a proximal section 21 has a third flexibility, a third lubricity, and a third length. In a preferred embodiment, the first length of the distal section 16 is 14.4 mm and the third length of the proximal section 21 is 5.5 mm. The overall length of this embodiment is 200 cm. As a result, the length of the distal section 16 is greater than the length of the proximal section 21, but less than the length of the central section 18.

The flexibility of the various sections 16, 18, and 21 is defined generally as the ability of that section to be bent back on itself along a radius without kinking. The smaller the radius, the greater the flexibility. By way of example, the flexibility of the distal section 16 is relatively great, in that it can be bent back on itself along a smaller radius than that of the proximal section 21. By comparison, the flexibility of the central section 18 is relatively great, in that it cannot be bent along a radius as small as that of the central section 18 without kinking. Accordingly, the flexibility of the proximal section 21 is less than that of the distal section 16, but greater than that of the central section 18.

The lubricity of the various sections 16, 18, and 21 is based generally on the coefficient of friction which exists between the materials forming the outer surface of the individual sections 16, 18, and 21, and the tissue forming the urinary conduit. Where this coefficient of friction is low, the associated sections 16, 18, and 21 are deemed to have a high lubricity facilitating insertion, but inhibiting retention of the guidewire 10 within the urinary tract. In the illustrated embodiment, the proximal section 21 is constructed to have a lubricity less than that of the distal section 16, but greater than that of the central section 18.

These characteristics of the present invention provide the urological guidewire 10 with performance far superior to that of previous guidewires. With the relatively high lubricity in the distal section, guidewire insertion is greatly facilitated; but with the relatively low lubricity in the central section 18, the tension of the guidewire 10 is greatly increased. In the proximal section 21, the medium level of lubricity is provided to facilitate the retrograde insertion of instruments over the guidewire 10.

The flexibility of the guidewire 10 is greatest in the distal section 16 and facilitates initial insertion of the guidewire 10 through the tortuous path of the urinary conduit. Once the distal section 16 is passed, the central section 18 with its reduced flexibility can tend to straighten the urinary canal and otherwise facilitate the insertion of instruments over the guidewire 10. A medium level of flexibility can be maintained in the proximal section 21 only as necessary to facilitate retrograde insertion of the guidewire 10 into the guidechannel of the instrument.

In combination, these features facilitate the initial insertion of the guidewire 10 with the relatively flexible and lubricious distal section 16, and the straightening of the urinary tract with the relatively inflexible central section 18.

The guidewire 10 tends to remain in place with the relatively non-lubricious characteristics of the central section 18. With medium levels of flexibility and lubricity in the proximal section 21, the guidewire 10 can be easily inserted into the guidelumen of the instrument. Further insertion of the instrument is facilitated by the relatively high coefficient of friction, which maintains the central section 18 in its operative position within the urinary tract.

These features are provided in a preferred embodiment with a construction that includes a core 23 having a distal end 25 and a proximal end 27. In a preferred embodiment, the core 23 is formed of a material having superelastic characteristics such as Nitinol. The core 23 has a constant diameter of 0.032 inches in the central section 18. At the distal end 25, the core 23 is provided with a taper 30, which is about 3 inches in length. The taper 30 reduces the diameter of the core 23 from 0.032 inches at the central section 18 to a diameter of 0.006 inches at a distal tip 32. The tip 32 in the preferred embodiment has a length of about 1.5 inches. In the distal section 16, the taper 30 and the distal tip 32 of the core 23 can be covered by a wire coil 34, which in a preferred embodiment is provided with a hydrophilic coating 36. In a preferred embodiment, the wire forming the coil 34 has a circular cross-section and a diameter of 0.005 inches.

This construction of the distal section 16 is of particular advantage to the guidewire 10, as it provides a high degree of flexibility at the distal end 14. In this preferred embodiment, the distal section 16 can be bent back on itself without kinking along a radius as small as 0.10 inches.

A similar construction can be provided in the proximal section 21, wherein the core 23 includes a taper 38 from the central section diameter of 0.032 inches to a diameter of about 0.010 inches. A flat-wire coil 41 can be formed over the taper 38 in the proximal section 21. Both of the wire coils 34 and 41 are preferably formed of a stainless steel.

In the guidewire constructions of the prior art, the core material is typically the same as the material forming the wire coils. As a consequence, the two materials are easily bonded chemically, using chemical bonding methods that attach the molecules of the core to the molecules of the coil. When the materials forming these two elements are dissimilar, chemical bonding may not be sufficiently reliable to ensure that the core 23 and coil 34 are maintained in a fixed relationship. Failure to maintain this relationship can result in undesirable separation of the coil 34 from the core 23.

In accordance with the present invention, a mechanical bond is formed between the core 23 and coil 34 to ensure that there is no separation between these structural elements. In accordance with the present invention, a mechanical interlock 43 is provided between the distal tip 32 of the core 23 at the distal end of the coil 34. This mechanical interlock 43 provides for a mechanical attachment of the core 23 to the coil 34 without the need for any chemical bond. This mechanical interlock 43 can be of the type illustrated in the axial cross-section view of FIG. 2. The concept of this embodiment requires a formation of an enlargement 45 at the distal tip 32 of the core 23. This enlargement 45 in the illustrated embodiment is formed by bending the tip 32 back on itself to form a hook 47. Whether provided in the hook configuration or any other shape, the enlargement 45 typically has a lateral or radial dimension that is greater than the diameter of the distal tip 32. This enlargement 45 can then be encased in a material capable of being set to form a plug 50 enclosing the enlargement 45 (such as the hook 47) and portions of the coil 34, as illustrated in FIG. 2. The plug 50 engages the enlargement 45 as well as the coil 34 to mechanically inhibit their separation. By providing the enlargement 45, the mechanical bond between the plug 50 and the core 23 is greatly enhanced.

The material forming the plug 50 can have a variety of characteristics, each offering some advantage in a particular embodiment of the invention. For example, the plug 50 can be formed from a solder such as silver solder, or from an adhesive such as an epoxy.

Figure 3:
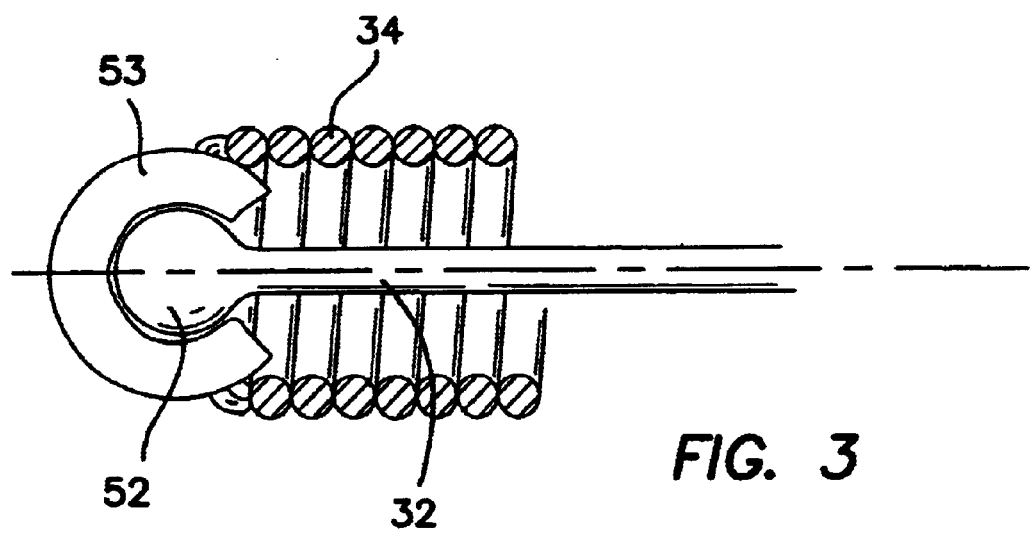
FIG. 3 is a side elevation view in axial cross section illustrating a boss crimped around an enlargement at the distal end of the core.
Figure 4:
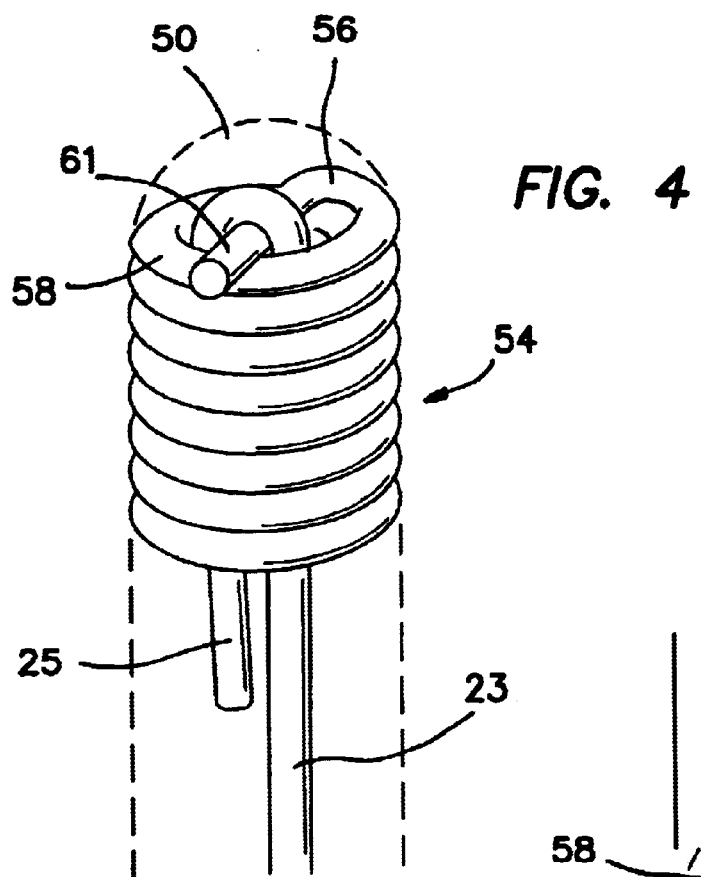
FIG. 4 is an enlarged perspective view of an additional embodiment of a mechanical interlock formed by bending the core over a bridge of the coil.
Figure 5:
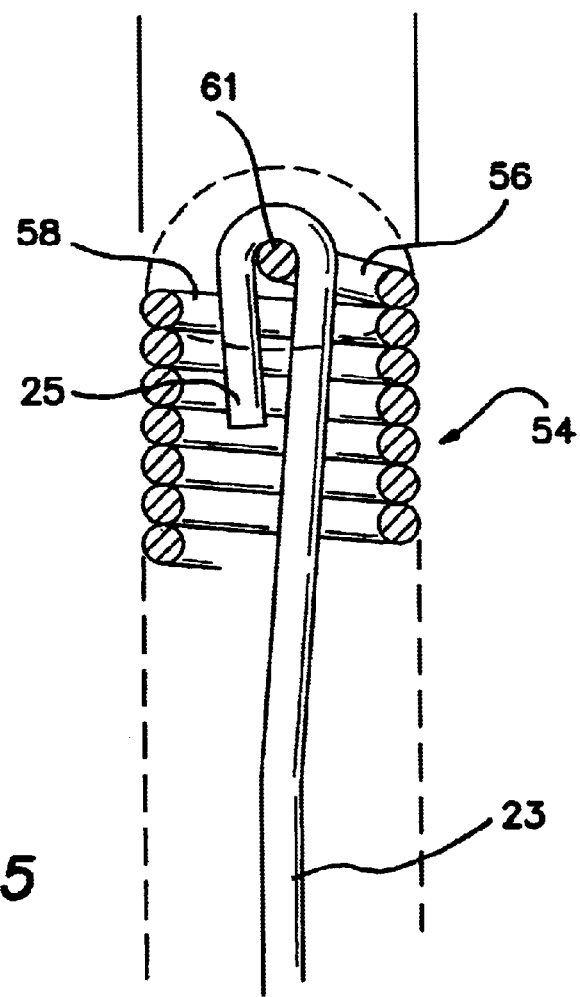
FIG. 5 is a radial cross section view of the embodiment illustrated in FIG. 3.

Another embodiment of the mechanical interlock 43 is illustrated in FIG. 3, wherein the enlargement 45 is provided in the shape of a sphere 52 and the mechanical interlock 43 is provided by a stainless steel boss 53, which is crimped over the sphere 52 and the distal end of the wire coil 34. This boss 53, which is typically formed of stainless steel, provides the mechanical interlock, not only with the sphere 52, but also with the wire coil 34, so that these two elements are held in a fixed, non-separable relationship.

Another embodiment of the mechanical interlock 43 is illustrated in FIGS. 4–8. In this embodiment, the wire coil 34 is formed with a plurality of convolutions 54, including an ultimate convolution 56 and a penultimate convolution 58. In this embodiment, the convolutions 54 have a generally constant diameter, except for the ultimate convolution 56. For example, with reference to FIG. 5, it can be seen that the convolutions 54 have a diameter D1, except for the ultimate convolution 56, which has a diameter D2 less than D1. With this lesser diameter D2, the distal tip 32 of the wire core forms a bridge 61 in the ultimate convolution 56, which extends across the penultimate convolution 58. With the coil 34 in this configuration, the distal tip 32 of the core 23 can be bent over the bridge 61 to form a portion of the mechanical interlock 43. This also forms the enlargement 45 in the shape of the hook 47, which can then be encased in the plug 50 to further enhance the properties of the mechanical interlock 43.

Figure 8:
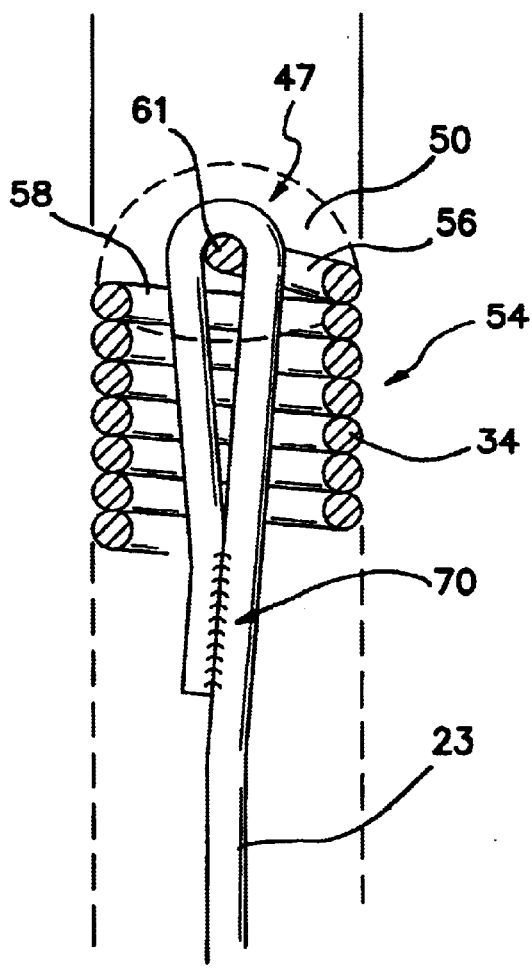
FIG. 8 is a side elevation view of a further embodiment of the distal end of the core bent back on itself and fixed to itself with a shear joint.

In order to even further enhance the properties of the mechanical interlock 43, the distal end 32 of the core 23, which is bent back on itself to form the hook 47, can be attached to itself, for example, as illustrated in FIGS. 6–8. More specifically, the distal tip 32 can be bent back on itself and attached to the core 23 by mechanical means such as a metal or plastic ferrule, or a clip 63. Alternatively, the distal tip 32 can be laser welded, for example, to form a butt joint 67, as illustrated in FIG. 7, or a shear joint 70, as shown in FIG. 8. In a further embodiment illustrated in FIG. 9, the distal tip 34 is bent back on itself and then fed through the plurality of convolutions 54 to further enhance the characteristics of the mechanical interlock 43.

Figure 9:
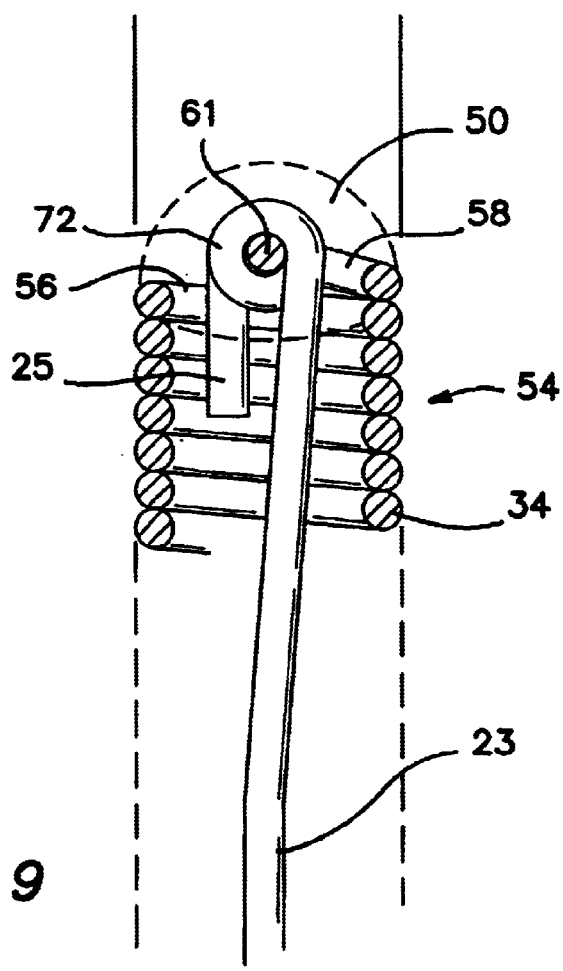
FIG. 9 is a perspective view of a further embodiment illustrating the core formed around the bridge and at least one revolution.

In still a further embodiment of the invention, the distal tip 32 of the core 23 can be wrapped around the bridge 61 in one or more revolutions designated by the reference numeral 72 in FIG. 9. This further enhances the mechanical attachment of the core 23 to the coil 34 and greatly increases the properties of the mechanical interlock 43.

Having reviewed certain preferred embodiments of the invention, many modifications will now be apparent and of particular advantage in other embodiments of the concept. For example, it will be noted that the bridge 61 can generally have any length; however, it may be desirable for the bridge 61 to have a length greater than the diameter D1 of the penultimate convolution 58. This ensures that the bridge 61 is supported at both of its ends by the penultimate convolution 58. It will also be noted that the bridge 61 can be formed generally in any of the convolutions 54, not just the ultimate convolution 56, in order to facilitate the mechanical interlock between the coil 34 and the core 23.

Although the foregoing embodiments and methods of operation have been described in significant detail, it will be apparent that this invention is a concept which may be otherwise embodied. As a result, one is cautioned not to determine the nature of the concept solely with reference to the described embodiments and method steps, but rather with particular reference to the following claims.

What is claimed is:

1. A urological guidewire, comprising:
   a core having a distal end with a diameter, the core being formed of a first metallic material and extending toward an end of the guidewire;
   a coil including a plurality of convolutions extending around the core at the end of the guidewire, the coil being formed of a second metallic material different from the first metallic material;
   a mechanical interlock having a bent portion formed between the coil and the core providing a mechanical attachment of the core to the coil, the mechanical interlock further comprising an enlargement having a fixed relationship with the end of the core and having a lateral dimension greater than the diameter of the core at the distal end of the core, and a bonding material fixing the enlargement to the coil to mechanically bond the core to the coil;
   a penultimate convolution included among the plurality of convolutions, the penultimate convolution having a first radius of curvature; and
   an ultimate convolution included among the plurality of convolutions, the ultimate convolution having a second radius of curvature less than the first radius of curvature to form a bridge across the penultimate convolution.

2. The urological guidewire recited in claim 1, wherein the enlargement is formed integral with the core and comprises a hook formed at the distal end of the core.

3. The urological guidewire recited in claim 1, wherein the mechanical interlock comprises:
   portions of the core extending at least partially around the bridge of the ultimate convolution to mechanically interlock the core and the coil of the guidewire.

4. The urological guidewire recited in claim 3, wherein the portions of the core include at least one revolution of the core extending around the bridge of the coil.

5. The urological guidewire recited in claim 4, wherein:
   the distal end of the core is bent back on itself; and
   the distal end of the core is attached to itself to fix the distal end of the core around the bridge of the coil.

6. The urological guidewire, comprising:
   a distal section having a first flexibility, a first lubricity, and a first length;
   a central section having a second flexibility, a second lubricity, and a second length;
   a proximate section having a third flexibility, a third lubricity, and a third length;
   the third flexibility being greater than the second flexibility and less than the first flexibility;
   the second lubricity and the third lubricity being less than the first lubricity; and
   the first length being greater than the third length and less than the second length.

7. A urological guidewire, comprising:
   a distal section having a first flexibility, a first lubricity and a first length;
   a central section having a second flexibility, a second lubricity and a second length; and
   a proximate section having a third flexibility, a third lubricity and a third length,
   wherein the third flexibility being greater than the second flexibility and less than the first flexibility, and
   wherein the second lubricity and the third lubricity being less than the first lubricity.

8. The urological guidewire recited in claim 7, wherein the first length is greater than the third length.

9. A urological guidewire, comprising:
   a distal section having a first flexibility, a first lubricity and a first length;
   a central section having a second flexibility, a second lubricity and a second length; and
   a proximate section having a third flexibility, a third lubricity and a third length,
   wherein the first flexibility being greater than the second flexibility and the third flexibility, and
   wherein the first lubricity being greater than the second lubricity and the third lubricity.

10. The urological guidewire recited in claim 9, wherein the third lubricity being greater than the second lubricity.

11. The urological guidewire recited in claim 9, wherein the first length is greater than the third length.

12. The urological guidewire recited in claim 11, wherein the first length is less than the second length.

* * * * *